US007332175B2

(12) United States Patent
Konetzki

(10) Patent No.: US 7,332,175 B2
(45) **Date of Patent: *Feb. 19, 2008**

(54) LONG-ACTING DRUG COMBINATIONS FOR THE TREATMENT OF RESPIRATORY COMPLAINTS

(75) Inventor: Ingo Konetzki, Warthausen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 257 days.

This patent is subject to a terminal disclaimer.

(21) Appl. No.: 10/826,048

(22) Filed: Apr. 16, 2004

(65) Prior Publication Data

US 2005/0004228 A1 Jan. 6, 2005

Related U.S. Application Data

(60) Provisional application No. 60/489,328, filed on Jul. 22, 2003.

(30) Foreign Application Priority Data

May 27, 2003 (DE) ................................ 103 23 966

(51) Int. Cl.

| | |
|---|---|
| ***A61K 9/00*** | (2006.01) |
| ***A61K 31/44*** | (2006.01) |
| ***A61K 31/18*** | (2006.01) |
| ***A01N 43/42*** | (2006.01) |
| ***A01N 41/06*** | (2006.01) |

(52) U.S. Cl. ....................... 424/400; 514/291; 514/602

(58) Field of Classification Search ................ 424/400; 514/291, 602

See application file for complete search history.

(56) References Cited

U.S. PATENT DOCUMENTS 6,706,726 B2 3/2004 Meissner et al.

(Continued)

FOREIGN PATENT DOCUMENTS

WO WO 02/32899 4/2002

(Continued)

*Primary Examiner*—Johann R. Richter
*Assistant Examiner*—Konata M. George
(74) *Attorney, Agent, or Firm*—Michael P. Morris; Mary-Ellen M. Devlin; Wendy Petka

(57) ABSTRACT

A pharmaceutical composition comprising:
(a) an anticholinergic of formula 1

1

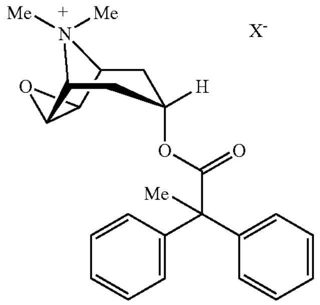

wherein $X^-$ is an anion with a single negative charge; and
(b) a compound of formula 2

2

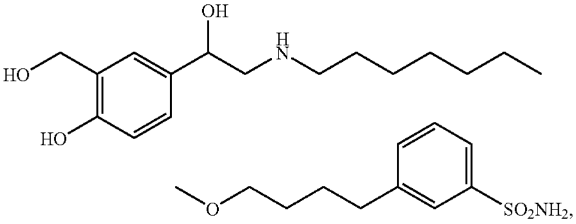

or the pharmacologically acceptable acid addition salts, solvates, and hydrates thereof.

18 Claims, 1 Drawing Sheet

U.S. PATENT DOCUMENTS

| | | | |
|---|---|---|---|
| 6,747,154 | B2 | 6/2004 | Brandenburg et al. |
| 2003/0223937 | A1 | 12/2003 | Banholzer et al. |
| 2004/0002502 | A1 | 1/2004 | Banholzer et al. |
| 2004/0010003 | A1 | 1/2004 | Banholzer et al. |
| 2004/0024007 | A1 | 2/2004 | Pairet et al. |
| 2004/0044020 | A1 | 3/2004 | Meade et al. |
| 2004/0048886 | A1 | 3/2004 | Meade et al. |
| 2004/0048887 | A1 | 3/2004 | Meade et al. |
| 2004/0058950 | A1 | 3/2004 | Meade et al. |
| 2004/0087617 | A1 | 5/2004 | Meissner et al. |
| 2004/0166065 | A1 | 8/2004 | Schmidt |
| 2004/0228805 | A1* | 11/2004 | Pieper et al. ................. 424/46 |
| 2005/0008578 | A1 | 1/2005 | Schmidt |
| 2005/0025718 | A1 | 2/2005 | Meade et al. |
| 2005/0101625 | A1 | 5/2005 | Boeck et al. |
| 2005/0154006 | A1 | 7/2005 | Meade et al. |
| 2005/0186175 | A1 | 8/2005 | Meade et al. |

FOREIGN PATENT DOCUMENTS

| | | |
|---|---|---|
| WO | WO 02/066422 | 8/2002 |

* cited by examiner

LONG-ACTING DRUG COMBINATIONS FOR THE TREATMENT OF RESPIRATORY COMPLAINTS

RELATED APPLICATIONS

This application claims benefit of U.S. Ser. No. 60/489,328, filed Jul. 22, 2003, and claims priority to German Application No. 103 23 966.9, filed May 27, 2003, each of which is hereby incorporated by reference in its entirety.

FIELD OF THE INVENTION

The present invention relates to novel pharmaceutical compositions based on a new anticholinergic and a new long-acting $\beta_2$-agonist, processes for the preparation thereof and the use thereof in the treatment of respiratory complaints.

SUMMARY OF THE INVENTION

The present invention relates to novel pharmaceutical compositions containing in addition to an anticholinergic of formula 1

1

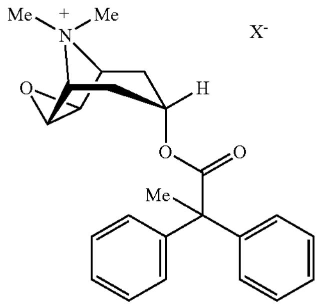

wherein:

$X^-$ denotes an anion with a single negative charge, preferably an anion selected from the group consisting of chloride, bromide, iodide, sulfate, phosphate, methanesulfonate, nitrate, maleate, acetate, citrate, fumarate, tartrate, oxalate, succinate, benzoate, and p-toluenesulfonate, the compound of formula 2

2

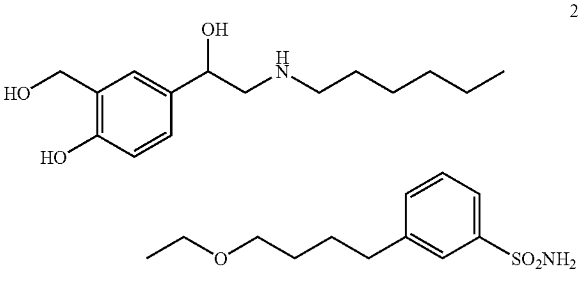

optionally in the form of the pharmacologically acceptable acid addition salts, and optionally in the form of the enantiomers, mixtures of enantiomers or racemates, and optionally in the form of the solvates and hydrates thereof, and optionally combined with physiologically acceptable excipients.

Preferably the salts of formula 1 are used wherein:

$X^-$ denotes an anion with a single negative charge, selected from the group consisting of chloride, bromide, 4-toluenesulfonate, and methanesulfonate, preferably bromide.

Particularly preferably the salts of formula 1 are used wherein:

$X^-$ denotes an anion with a single negative charge, selected from the group consisting of chloride, bromide, and methanesulfonate, preferably bromide.

Particularly preferred according to the invention is the salt of formula 1, wherein $X^-$ denotes bromide.

The compounds of formula 1 are known from WO 02/32899.

Surprisingly, an unexpectedly beneficial therapeutic effect, particularly a synergistic effect, can be observed in the treatment of inflammatory or obstructive diseases of the respiratory tract if the anticholinergic of formula 1 is administered together with the compound of formula 2. In view of this synergistic effect, the drug combinations according to the invention can be used in smaller doses than would be the case with the individual compounds used in monotherapy in the usual way. As another positive aspect of the present invention, this reduces unwanted side effects such as may occur when betamimetics are administered, for example. Unwanted side effects which deserve special mention in this context are the stimulant effects on the heart which may be caused by betamimetics, particularly tachycardia, a stronger heartbeat, pain resembling angina pectoris, as well as arrhythmia.

The abovementioned effects are observed both when the two active substances are administered simultaneously in a single active substance formulation and also when the two active substances are administered successively in separate formulations. It is preferred according to the invention to administer the two active substance components simultaneously in a single formulation.

DESCRIPTION OF THE INVENTION

Figure 1:
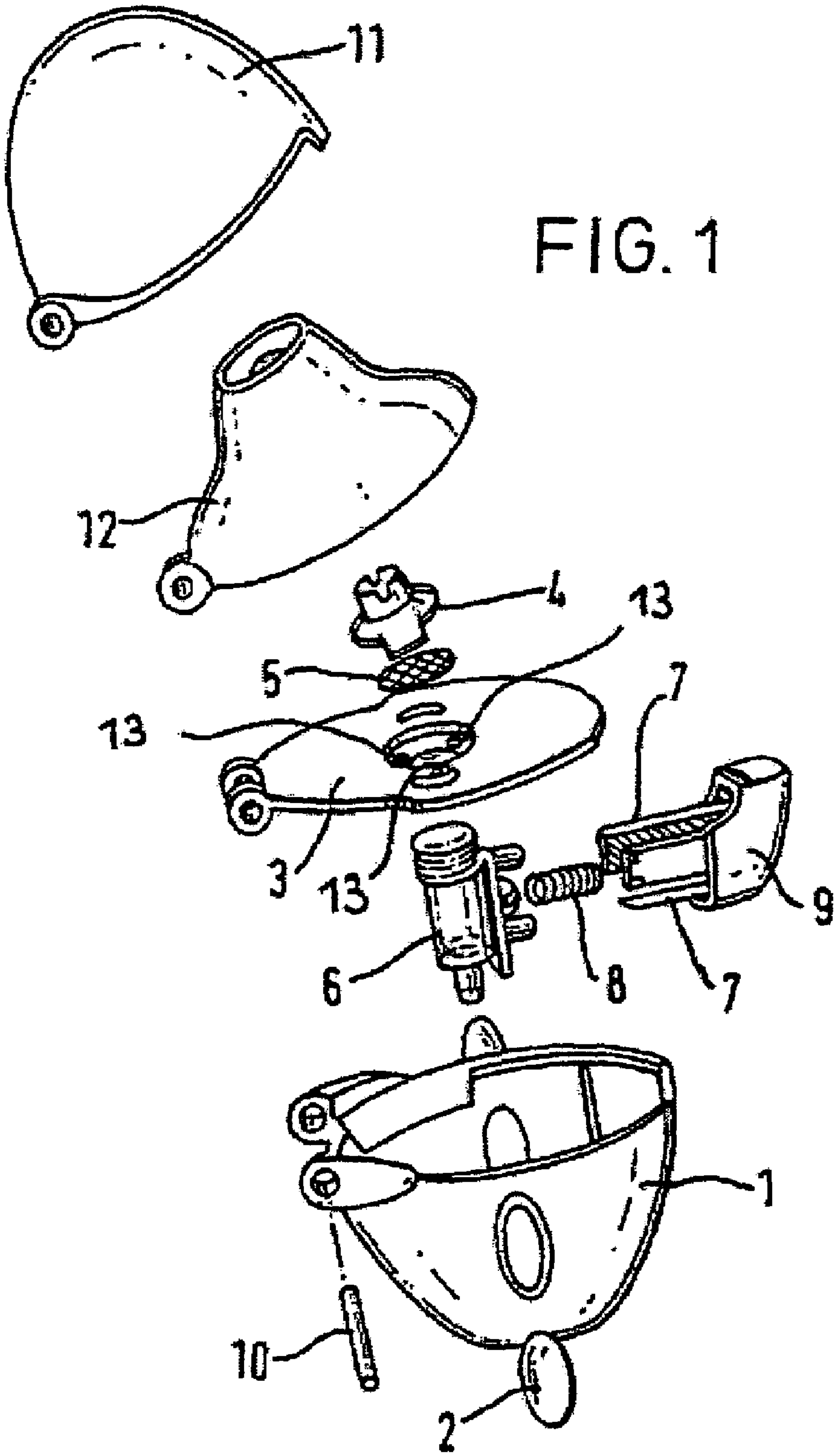
FIG. 1 illustrates a particularly preferred inhaler device (sold under the trademark HANDIHALER®) for administering the pharmaceutical combination according to the invention in inhalettes.

Any reference to the compound 1' within the scope of the present invention is to be regarded as a reference to the pharmacologically active cation of the following formula contained in the salts 1:

1'

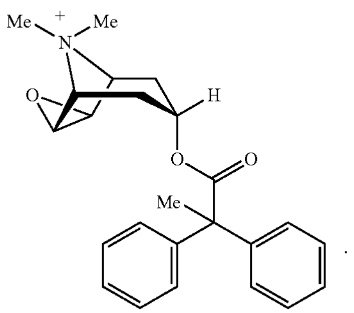

In the abovementioned drug combinations, the active substances may either both be contained in a single formulation or may be contained in two separate formulations. Pharmaceutical compositions which contain the active substances 1 and 2 in a single formulation are preferred according to the invention.

Any reference to the betamimetic of formula 2 includes a reference to the enantiomers (R or S) or the mixtures thereof, the R-enantiomer of the compound being of particular importance within the scope of the present invention. Process for the enantioselective preparation of the enantiomers of the compound of formula 2 are known in the art. The compound 2 may also be present according to the invention in the form of its salts, as well as its hydrates or solvates.

Within the scope of the present invention, the reference to compound 2 includes a reference to the physiologically acceptable acid addition salts thereof. By physiologically acceptable acid addition salts of the betamimetics 2 are meant according to the invention pharmaceutically acceptable salts which are selected from the salts of hydrochloric acid, hydrobromic acid, sulfuric acid, phosphoric acid, methanesulfonic acid, acetic acid, fumaric acid, succinic acid, lactic acid, citric acid, tartaric acid, 1-hydroxy-2-naphthalenecarboxylic acid, or maleic acid. If desired, mixtures of the above-mentioned acids may be used to prepare the salts 2. According to the invention, the salts of 2 selected from among the hydrochloride, hydrobromide, sulfate, phosphate, fumarate, methanesulfonate, maleate, and xinafoate are preferred.

In one aspect, the present invention relates to the abovementioned pharmaceutical compositions which contain, in addition to therapeutically effective quantities of 1 and 2, a pharmaceutically acceptable excipient. In another aspect, the present invention relates to the abovementioned pharmaceutical compositions which do not contain any pharmaceutically acceptable excipient in addition to therapeutically effective quantities of 1 and 2.

The present invention further relates to the use of therapeutically effective amounts of the salts 1 for preparing a pharmaceutical composition which also contains the compound of formula 2 for the treatment of inflammatory or obstructive respiratory complaints. Preferably the present invention relates to the abovementioned use for preparing a pharmaceutical composition for the treatment of asthma or COPD.

Within the scope of the present invention, the compounds 1 and 2 may be administered simultaneously or one after the other; preferably, the compounds 1 and 2 are administered simultaneously according to the invention.

The present invention also relates to the use of therapeutically effective quantities of salts 1 and long-acting betamimetics 2 for the treatment of inflammatory or obstructive respiratory complaints, particularly asthma or COPD.

The proportions in which the active substances 1 and 2 may be used in the active substance combinations according to the invention are variable. Active substances 1 and 2 may possibly be present in the form of their solvates or hydrates. Depending on the choice of the salts 1 and 2, the weight ratios which may be used within the scope of the present invention vary on the basis of the different molecular weights of the various salt forms. Therefore the following ratios by weight are based on the cation 1' and the free base of the compound 2.

The active substance combinations according to the invention may contain 1' and the free base of the compound of formula 2 in ratios by weight ranging, for example, from about 1:30 to 400:1, preferably 1:25 to 200:1, preferably 1:20 to 100:1, particularly preferably from 1:15 to 50:1.

For example, without restricting the scope of the invention thereto, preferred combinations of 1 and 2 according to the invention may contain the cation 1' and the free base of the compound 2 in the following proportions by weight: 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, or 35:1.

The pharmaceutical compositions according to the invention containing the combinations of 1 and 2 are normally administered so that the cation 1' and the compound 2 are present together in doses of 5 μg to 5000 μg, preferably from 10 μg to 2000 μg, more preferably from 15 μg to 1000 μg, even more preferably from 20 μg to 800 Fug, preferably according to the invention from 30 μg to 750 μg, preferably from 40 μg to 700 μg, per single dose, these total dosages being based on the free base of compound 2.

For example, combinations of 1 and 2 according to the invention contain a quantity of 1' and compound of formula 2 such that the total dosage per single dose is about 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, 160 μg, 165 μg, 170 μg, 175 μg, 180 μg, 185 μg, 190 μg, 195 μg, 200 μg, 205 μg, 210 μg, 215 μg, 220 μg, 225 μg, 230 μg, 235 μg, 240 μg, 245 μg, 250 μg, 255 μg, 260 μg, 265 μg, 270 μg, 275 μg, 280 μg, 285 μg, 290 μg, 295 μg, 300 μg, 305 μg, 310 μg, 315 μg, 320 μg, 325 μg, 330 μg, 335 μg, 340 μg, 345 μg, 350 μg, 355 μg, 360 μg, 365 μg, 370 μg, 375 μg, 380 μg, 385 μg, 390 μg, 395 μg, 400 μg, 405 μg, 410 μg, 415 μg, 420 μg, 425 μg, 430 μg, 435 μg, 440 μg, 445 μg, 450 μg, 455 μg, 460 μg, 465 μg, 470 μg, 475 μg, 480 μg, 485 μg, 490 μg, 495 μg, 500 μg, 505 μg, 510 μg, 515 μg, 520 μg, 525 μg, 530 μg, 535 μg, 540 μg, 545 μg, 550 μg, 555 μg, 560 μg, 565 μg, 570 μg, 575 μg, 580 μg, 585 μg, 590 μg, 595 μg, 600 μg, 605 μg, 610 μg, 615 μg, 620 μg, 625 μg, 630 μg, 635 μg, 640 μg, 645 μg, 650 μg, 655 μg, 660 μg, 665 μg, 670 μg, 675 μg, 680 μg, 685 μg, 690 μg, 695 μg, 700 μg, or the like. Here, too, the dosages specified are based on the content of free base of the compound 2 in the drug combinations according to the invention. It is clear to the skilled person that these proposed dosages per single dose are not to be regarded as being restricted to the numerical values explicitly mentioned. Fluctuations of around ±2.5 μg, particularly fluctuations in the decimal range, are also covered as will be apparent to anyone skilled in the art. In these dosage ranges the active substances 1' and 2 may be present in the weight ratios described above.

The active substance combinations of 1 and 2 according to the invention are preferably administered by inhalation. For this purpose, ingredients 1 and 2 have to be made available in forms suitable for inhalation. Inhalable preparations include inhalable powders, propellant-containing metering aerosols, or propellant-free inhalable solutions. Inhalable powders according to the invention containing the combination of active substances 1 and 2 may consist of the active substances on their own or of a mixture of the active substances with physiologically acceptable excipients. Within the scope of the present invention, the term propellant-free inhalable solutions also includes concentrates or sterile inhalable solutions ready for use. The preparations according to the invention may contain the combination of active substances 1 and 2 either together in one formulation or in two separate formulations. These formulations which may be used within the scope of the present invention are described in more detail in the next part of the specification.

A. Inhalable Powder Containing the Combinations of Active Substances 1 and 2 According to the Invention The inhalable powders according to the invention may contain 1 and 2 either on their own or in admixture with suitable physiologically acceptable excipients. If the active substances 1 and 2 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, maltose, or trehalose), oligo- and polysaccharides (e.g., dextrans), polyalcohols (e.g., sorbitol, mannitol, or xylitol), salts (e.g., sodium chloride or calcium carbonate) or mixtures of these excipients. Preferably, mono- or disaccharides are used, while the use of lactose or glucose is preferred, particularly, but not exclusively, in the form of their hydrates.

Within the scope of the inhalable powders according to the invention the excipients have a maximum average particle size of up to 250 μm, preferably between 10 μm and 150 μm, most preferably between 15 μm and 80 μm. It may sometimes seem appropriate to add finer excipient fractions with an average particle size of 1 μm to 9 μm to the excipients mentioned above. These finer excipients are also selected from the group of possible excipients listed hereinbefore. Finally, in order to prepare the inhalable powders according to the invention, micronized active substance 1 and 2, preferably with an average particle size of 0.5 μm to 10 μm, more preferably from 1 μm to 5 μm, is added to the excipient mixture. Processes for producing the inhalable powders according to the invention by grinding and micronizing and lastly mixing the ingredients together are known from the prior art. The inhalable powders according to the invention may be prepared and administered either in the form of a single powder mixture which contains both 1 and 2 or in the form of separate inhalable powders which contain only 1 or 2.

The inhalable powders according to the invention may be administered using inhalers known from the prior art. Inhalable powders according to the invention which contain a physiologically acceptable excipient in addition to 1 and 2 may be administered, for example, by means of inhalers which deliver a single dose from a supply using a measuring chamber as described in U.S. Pat. No. 4,570,630, or by other means as described in DE 36 25 685 A. The inhalable powders according to the invention which contain 1 and 2 optionally in conjunction with a physiologically acceptable excipient may be administered, for example, using the inhaler sold under the trademark TURBUHALER® or using inhalers as disclosed for example in EP 237507 A. Preferably, the inhalable powders according to the invention which contain physiologically acceptable excipient in addition to 1 and 2 are packed into capsules (to produce so-called inhalettes) which are used in inhalers as described, for example, in WO 94/28958 (corresponding to U.S. Pat. No. 5,947,118, which is hereby incorporated by reference).

A particularly preferred inhaler for administering the pharmaceutical combination according to the invention in inhalettes is shown in FIG. 1. This inhaler (sold under the trademark HANDIHALER®) for inhaling powdered pharmaceutical compositions from capsules is characterized by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut and air holes 13 for adjusting the flow resistance.

B. Propellant Gas-Driven Inhalation Aerosols Containing the Combinations of Active Substances 1 and 2

Inhalation aerosols containing propellant gas according to the invention may contain substances 1 and 2 dissolved in the propellant gas or in dispersed form. 1 and 2 may be present in separate formulations or in a single preparation, in which 1 and 2 are either both dissolved, both dispersed, or only one component is dissolved and the other is dispersed. The propellant gases which may be used to prepare the inhalation aerosols according to the invention are known from the prior art. Suitable propellant gases are selected from among hydrocarbons such as n-propane, n-butane, or isobutane and halohydrocarbons such as preferably chlorinated and fluorinated derivatives of methane, ethane, propane, butane, cyclopropane, or cyclobutane. The propellant gases mentioned above may be used on their own or in mixtures thereof. Particularly preferred propellant gases are halogenated alkane derivatives selected from TG11, TG12, TG134a (1,1,1,2-tetrafluoroethane), TG227 (1,1,1,2,3,3,3-heptafluoropropane), and mixtures thereof, the propellant gases TG134a, TG227, and mixtures thereof being preferred.

The propellant-driven inhalation aerosols according to the invention may also contain other ingredients such as cosolvents, stabilizers, surfactants, antioxidants, lubricants, and pH adjusters. All these ingredients are known in the art.

The inhalation aerosols containing propellant gas according to the invention may contain up to 5 wt.-% of active substance 1 and/or 2. Aerosols according to the invention contain, for example, 0.002 to 5 wt.-%, 0.01 to 3 wt.-%, 0.015 to 2 wt.-%, 0.1 to 2 wt.-%, 0.5 to 2 wt.-% or 0.5 to 1 wt.-% of active substance 1 and/or 2.

If the active substances 1 and/or 2 are present in dispersed form, the particles of active substance preferably have an average particle size of up to 10 μm, preferably from 0.1 μm to 6 μm, more preferably from 1 μm to 5 μm.

The propellant-driven inhalation aerosols according to the invention mentioned above may be administered using inhalers known in the art, such as metered dose inhalers (MDIs). Accordingly, in another aspect, the present invention relates to pharmaceutical compositions in the form of propellant-driven aerosols as hereinbefore described combined with one or more inhalers suitable for administering these aerosols. In addition, the present invention relates to inhalers which are characterized in that they contain the propellant gas-containing aerosols described above according to the invention. The present invention also relates to cartridges which are fitted with a suitable valve and can be used in a suitable inhaler and which contain one of the abovementioned propellant gas-containing inhalation aerosols according to the invention. Suitable cartridges and methods of filling these cartridges with the inhalable aerosols containing propellant gas according to the invention are known from the prior art.

C. Propellant-Free Inhalable Solutions or Suspensions Containing the Combinations of Active Substances 1 and 2 According to the Invention Propellant-free inhalable solutions according to the invention contain, for example, aqueous or alcoholic, preferably ethanolic solvents, possibly ethanolic solvents in admixture with aqueous solvents. In the case of aqueous/ethanolic solvent mixtures, the relative proportion of ethanol to water is not restricted, but the maximum limit is up to 70 percent by volume, more particularly up to 60 percent by volume of ethanol. The remainder of the volume is made up of water. The solutions or suspensions containing 1 and 2, separately or together, are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid etc. Preferred inorganic acids are hydrochloric acid and sulfuric acid. It is also possible to use the acids which have already formed an acid addition salt with one of the active substances. Of the organic acids, ascorbic acid, fumaric acid, and citric acid are preferred. If desired, mixtures of the above acids may also be used, particularly in the case of acids which have other properties in addition to their acidifying qualities, e.g., as flavorings, antioxidants, or complexing agents, such as citric acid or ascorbic acid, for example. According to the invention, it is particularly preferred to use hydrochloric acid to adjust the pH.

According to the invention, the addition of edetic acid (EDTA) or one of the known salts thereof, sodium edetate, as stabilizer or complexing agent is unnecessary in the present formulation. Other embodiments may contain this compound or these compounds. In a preferred embodiment, the content based on sodium edetate is less than 100 mg/100 mL, preferably less than 50 mg/100 mL, more preferably less than 20 mg/100 mL. Generally, inhalable solutions in which the content of sodium edetate is from 0 to 10 mg/100 mL are preferred.

Cosolvents and/or other excipients may be added to the propellant-free inhalable solutions according to the invention. Preferred cosolvents are those which contain hydroxyl groups or other polar groups, e.g., alcohols—particularly isopropyl alcohol, glycols—particularly propyleneglycol, polyethyleneglycol, polypropylene glycol, glycol ether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants, and/or preservatives which guarantee or prolong the shelf life of the finished pharmaceutical formulation, flavorings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those which are known in the art, particularly cetyl pyridinium chloride, benzalkonium chloride, or benzoic acid or benzoates such as sodium benzoate in the concentration known from the prior art. The preservatives mentioned above are preferably present in concentrations of up to 50 mg/100 mL, more preferably between 5 and 20 mg/100 mL.

Preferred formulations contain, in addition to the solvent water and the combination of active substances 1 and 2, only benzalkonium chloride and sodium edetate. In another preferred embodiment, no sodium edetate is present.

The propellant-free inhalable solutions according to the invention are administered in particular using inhalers of the kind which are capable of nebulizing a small amount of a liquid formulation in the therapeutic dose within a few seconds to produce an aerosol suitable for therapeutic inhalation. Within the scope of the present invention, preferred inhalers are those in which a quantity of less than 100 μL, preferably less than 50 μL, more preferably between 10 μL and 30 μL of active substance solution can be nebulized in preferably one spray action to form an aerosol with an average particle size of less than 20 μm, preferably less than 10 μm, such that the inhalable part of the aerosol corresponds to the therapeutically effective quantity.

An apparatus of this kind for propellant-free delivery of a metered quantity of a liquid pharmaceutical composition for inhalation is described for example in International Patent Application WO 91/14468 (corresponding to U.S. Pat. No. 5,497,944, which is hereby incorporated by reference) and also in WO 97/12687 (cf in particular FIGS. 6*a* and 6*b*) (corresponding to U.S. Pat. No. 5,964,416, which is hereby incorporated by reference). The nebulizers (devices) described therein are sold under the trademark RESPIMAT®. This RESPIMAT® nebulizer can advantageously be used to produce the inhalable aerosols according to the invention containing the combination of active substances 1 and 2.

Accordingly, in a further aspect, the invention relates to pharmaceutical formulations in the form of propellant-free inhalable solutions or suspensions as described above combined with a device suitable for administering these formulations, preferably in conjunction with the RESPIMAT® nebulizer. Preferably, the invention relates to propellant-free inhalable solutions or suspensions characterized by the combination of active substances 1 and 2 according to the invention in conjunction with the RESPIMAT® nebulizer. In addition, the present invention relates to the abovementioned devices for inhalation, preferably the RESPIMAT® nebulizer, characterized in that they contain the propellant-free inhalable solutions or suspensions according to the invention as described hereinbefore.

According to the invention, inhalable solutions which contain the active substances 1 and 2 in a single preparation are preferred. The term "single preparation" also includes preparations which contain the two ingredients 1 and 2 in two-chamber cartridges, as disclosed, for example, in WO 00/23037 (corresponding to U.S. Pat. No. 6,481,435), both of which are hereby incorporated by reference in their entireties.

The propellant-free inhalable solutions or suspensions according to the invention may take the form of concentrates or sterile inhalable solutions or suspensions ready for use, as well as the abovementioned solutions and suspensions designed for use in a RESPIMAT® nebulizer. Formulations ready for use may be produced from the concentrates, for example, by the addition of isotonic saline solutions. Sterile formulations ready for use may be administered using energy-operated fixed or portable nebulizers which produce inhalable aerosols by means of ultrasound or compressed air by the Venturi principle or other principles.

Accordingly, in another aspect, the present invention relates to pharmaceutical compositions in the form of propellant-free inhalable solutions or suspensions as described hereinbefore which take the form of concentrates or sterile formulations ready for use, combined with a device suitable for administering these solutions, characterized in that the device is an energy-operated free-standing or portable nebulizer which produces inhalable aerosols by means of ultrasound or compressed air by the Venturi principle or other methods.

The Examples which follow serve to illustrate the present invention in more detail without restricting the scope of the invention to the following embodiments by way of example. The following examples of formulations which may be obtained analogously to methods known in the art serve to illustrate the invention still further without restricting the scope of the invention thereto.

EXAMPLES OF FORMULATIONS

A. Inhalable Powder

1)

| ingredients | μg per capsule |
|---|---|
| 1'-bromide | 200 |
| 2 (hydrochloride) | 25 |
| lactose | 24775 |
| total | 25000 |

2)

| ingredients | μg per capsule |
|---|---|
| 1'-bromide | 100 |
| 2 (hydrochloride) | 50 |
| lactose | 12350 |
| total | 12500 |

3)

| ingredients | μg per capsule |
|---|---|
| 1'-bromide | 200 |
| 2 (fumaric acid salt) | 50 |
| lactose | 12250 |
| total | 12500 |

4)

| ingredients | μg per capsule |
|---|---|
| 1'-bromide | 200 |
| 2 (maleic acid salt) | 24 |
| lactose | 24776 |
| total | 25000 |

I claim:

1. A pharmaceutical composition comprising:

(a) an anticholinergic of formula 1

1

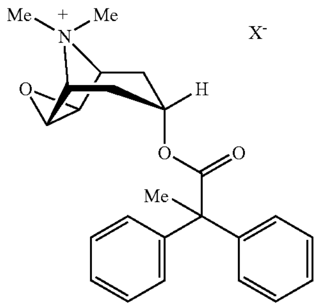

wherein $X^-$ is an anion with a single negative charge; and (b) a compound of formula 2

2

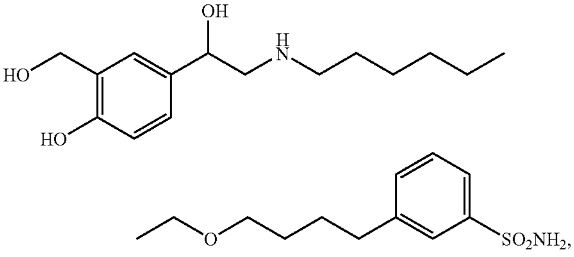

or the pharmacologically acceptable acid addition salts, solvates, and hydrates thereof.

2. The pharmaceutical composition according to claim 1, wherein $X^-$ is chloride, bromide, iodide, sulfate, phosphate, methanesulfonate, nitrate, maleate, acetate, citrate, fumarate, tartrate, oxalate, succinate, benzoate, or p-toluenesulfonate.

3. The pharmaceutical composition according to claim 1, further comprising a physiologically acceptable excipient.

4. The pharmaceutical composition according to claim 1, wherein the compound 2 is a salt of hydrochloric acid, hydrobromic acid, sulfuric acid, phosphoric acid, methanesulfonic acid, acetic acid, fumaric acid, succinic acid, lactic acid, citric acid, tartaric acid, 1-hydroxy-2-naphthalenecarboxylic acid, or maleic acid.

5. The pharmaceutical composition according to claim 1, wherein the compound 2 is an R-enantiomer, at least partially separated from the S-enantiomer.

6. The pharmaceutical composition according to one of claims 1 to 4, wherein the weight ratio of 1 '

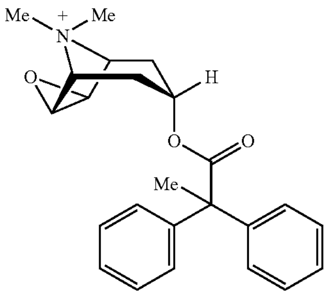

1' to 2 (based on the free base) is in the range from about 1:30 to about 400:1.

7. The pharmaceutical composition according to claim 6, wherein the weight ratio of 1' to 2 (based on the free base) is in the range from about 1:25 to about 200:1.

8. The pharmaceutical composition according to one of claims 1 to 5, wherein the pharmaceutical composition is suitable for inhalation.

9. The pharmaceutical composition according to claim 8, wherein the pharmaceutical composition is an inhalable powder, propellant-driven metered dose aerosol, or propellant-free inhalable solution.

10. The pharmaceutical composition according to claim 8, wherein the pharmaceutical composition is an inhalable powder including a physiologically acceptable excipient selected from monosaccharides, disaccharides, oligo- and polysaccharides, polyalcohols, salts, or mixtures thereof.

11. The pharmaceutical composition according to one of claims 1, 2, or 5, wherein the pharmaceutical composition is an inhalable powder containing the compounds 1 and 2 as its sole ingredients.

12. The pharmaceutical composition according to claim 8, wherein the pharmaceutical composition is a propellant-containing inhalable aerosol containing the compounds 1 and 2 in dissolved or dispersed form.

13. The propellant-containing inhalable aerosol according to claim 12, wherein the propellant gas is a hydrocarbon or halohydrocarbon.

14. The propellant-containing inhalable aerosol according to claim 12, wherein the propellant gas is n-propane, n-butane, or isobutane, or a chlorinated and/or fluorinated derivative of methane, ethane, propane, butane, cyclopropane, or cyclobutane, or a mixture thereof.

15. The propellant-containing inhalable aerosol according to claim 12, wherein the propellant gas is TG11, TG12, TG134a, TG227, or a mixture thereof.

16. The pharmaceutical composition according to claim 8, wherein the pharmaceutical composition is a propellant-free inhalable solution containing water, ethanol, or a mixture thereof as solvent.

17. The pharmaceutical composition according to claim 16, further comprising a cosolvent and/or excipient.

18. The pharmaceutical composition according to claim 1, wherein anticholinergics of formula 1 and compounds of formula 2 are substantially the sole active ingredients in the composition.

* * * * *